(12) United States Patent
Blumenkopf et al.

(10) Patent No.: US 6,635,762 B1
(45) Date of Patent: Oct. 21, 2003

(54) MONOCYCLIC-7H-PYRROLO[2,3-D] PYRIMIDINE COMPOUNDS, COMPOSITIONS, AND METHODS OF USE

(75) Inventors: Todd A. Blumenkopf, Old Lyme, CT (US); Mark E. Flanagan, Gales Ferry, CT (US); Matthew F. Brown, Pawcatuck, CT (US); Paul S. Changelian, E. Greenwich, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/335,030

(22) Filed: Jun. 17, 1999

Related U.S. Application Data
(60) Provisional application No. 60/089,886, filed on Jun. 19, 1998.

(51) Int. Cl.[7] .................... C07D 487/04; A61K 31/519; A61P 35/00; A61P 25/28; A61P 11/06
(52) U.S. Cl. .................. 544/280; 540/481; 540/600; 544/61; 544/117
(58) Field of Search ................ 544/293, 280, 544/117, 61; 514/265.1, 234.2, 228.5

(56) References Cited

U.S. PATENT DOCUMENTS

| | | | | |
|---|---|---|---|---|
| 5,389,509 | A | 2/1995 | Maskasky | 430/567 |
| 5,686,457 | A | 11/1997 | Traxler et al. | 514/258 |
| 6,080,747 | A | 6/2000 | Uckun et al. | 514/259 |
| 6,136,595 | A | 10/2000 | Ihle et al. | 435/320 |
| 6,180,636 | B1 | 1/2001 | Traxler et al. | 514/258 |
| 6,187,552 | B1 | 2/2001 | Roberds et al. | 435/7.93 |
| 6,310,063 | B1 * | 10/2001 | Ge et al. | 544/280 |
| 2003/0036545 | A1 * | 2/2003 | Castelhano | 544/280 |
| 2003/0045536 | A1 * | 3/2003 | Castelhano | 544/280 |
| 2003/0073708 | A1 * | 4/2003 | Castelhano | 544/280 |

FOREIGN PATENT DOCUMENTS

| | | | |
|---|---|---|---|
| EP | 0795556 | 9/1997 | |
| EP | 0682027 | 10/1997 | ......... C07D/487/04 |
| WO | 9320078 | * 10/1993 | |
| WO | WO9519774 | 7/1995 | |
| WO | WO9713771 | 10/1995 | |
| WO | WO9802437 | 7/1996 | |
| WO | WO9802438 | 7/1996 | |
| WO | WO9640142 | 12/1996 | |
| WO | WO9702262 | 1/1997 | ......... C07D/401/12 |
| WO | WO9702266 | 1/1997 | |
| WO | WO9718212 | 5/1997 | |
| WO | WO9727199 | 7/1997 | |
| WO | WO9728161 | 8/1997 | |
| WO | WO9732879 | 9/1997 | |
| WO | WO9749706 | 12/1997 | |
| WO | WO9807726 | 2/1998 | |
| WO | WO9823613 | 6/1998 | |
| WO | WO9833798 | 8/1998 | |
| WO | WO9951599 | 10/1999 | |
| WO | WO 9961428 | 12/1999 | |
| WO | WO9965908 | 12/1999 | ......... C07D/487/04 |
| WO | 9965909 | * 12/1999 | |
| WO | WO9965909 | 12/1999 | ......... C07D/487/04 |
| WO | WO0000202 | 1/2000 | |
| WO | WO0017203 | 3/2000 | ......... C07D/487/04 |
| WO | WO0142246 | 6/2001 | ......... C07D/487/04 |

OTHER PUBLICATIONS

Munoz, CMAJ 2000;162:65–72.*
Traxler, P. M., *Protein tyrosine kinase inhibitors in cancer treatment*, Exp. Opin. Ther. Patents, (1997) 7(6): 571–588.
Traxler, P. M. et al., *4–(phenylamino)pyrroloprimidines: Potent and Selective, ATP Site Directed Inhibitors of the EGF–Receptor Protein Tyrosine Kinase*, J. Med. Chem., 1996, 39, 2285–2292.
Johnson, et al., *Phosphorylation and activation of the Jak–3 Janus Kinase in response to Interleukin–2*, Nature, 370, 151 (1994).
S.M. Russell, et al., *Interaction of IL–2Rβ and γc Chains with Jak1 and Jak3: Implications for XSCID and XCID*, Science, 266, 1042 (1994).
J. N. Ihle, *The Janus Protein Tyrosine Kinase Family and its Role in Cytokine Signaling*, Adv. Immunology, 60, 1, (1995).
J. N. Ihle, *The Janus Protein Tyrosine Kinases in hematopoietic cytokine signaling*, Semin. Immunology, 7, 247, (1995).
T. Musso, et al., *Regulation of JAK3 Expression in Human Monocytes: Phosphorylation in Response to Interleukings 2, 4, and 7*, J. Exp. Med., 181, 1425 (1995).
R. A. Kirken, et al., *Activation of JAK3, but not JAK1, is critical for IL–2–induced proliferation and STAT5 Recruitment by a COOH–terminal region of the IL–2 receptor β–chain*, Cytokine, 7 689 (1995).
M. G. Malabarba, et al., *Activation of JAK3, but not JAK1, is Critical to Interleukin–4 (IL4) Stimulated Proliferation and Requires a Membrane–proximal Region of IL4 Receptor α**, J. Biol. Chem., 270, 9630, (1995).
J. H. Hanke, B. A. Pollok, and P. S. Changelian, *Role of tyrosine kinases in lymphocyte activation: Targets for drug intervention*, Inflamm. Res., 44, 357, (1995).
E.E. Eynon, et al., *Disruption of Cytokine Signaling in Lymphoid Development: Unique Contributions of the Common Cytokine Gamma Chain and the JAK3 Kinase*, J. Interferon Cytokine Res., 16, 677, (1996).
S. A. Oakes, et al., *Signaling via IL–2 and IL–4 in JAK#–Deficient Severe Combined Immunodeficiency Lymphocytes: JAK3–Dependent and Independent Pathways*, Immunity, 5, 605 (1996).

(List continued on next page.)

Primary Examiner—Mark L Berch
(74) Attorney, Agent, or Firm—Peter C. Richardson; Gregg C. Benson; Christine S. Lee

(57) ABSTRACT

Novel pyrrolo[2,3-d]pyrimidine compounds useful as inhibitors of the enzyme protein tyrosine kinases such as Janus Kinase 3 as well as immunosuppressive agents for organ transplants, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other autoimmune diseases are described.

3 Claims, No Drawings

OTHER PUBLICATIONS

L. D. Norangelo, et al, *Severe Combined Immune Deficiency due to Defects of the JAK3 Tyrosine Kinase*, Prog. Immunodeficiency, 6, 61, (1996).

D. C. Thomis, et al., *Peripheral Expression of JAK3 is Required to Maintain T Lymphocyte Function*, J. Exp. Med., 185, 197, (1997).

B. H. Nelson, et al., *Requirement for an initial signal from the membrane–proximal region of the interleukin 2 receptor γc chain for Janus kinase activation leading to T cell proliferation*, Proc. Natl. Acad. Sci. USA, 94, 1878, (1997).

K. D. Liu, et al., *JAK/STAT signaling by cytokine receptors*, Curr. Opin. Immunol.

W. J. Leonard and J. J. O'Shea, *JAKS and STATS: Biological Implications*, Annu. Rev. Immunol., 16, 293, (1998).

F. Cardotti, et al., *Severe combined immune deficiences due to defects in the common γ chain–JAK3 signaling pathway*, Springer Semin. Immuopathol., 19, 401, (1998).

R. Malaviya, et al., *Targeting Janus Kinase 3 in Mast Cells Prevents Immediate Hypersensitivity Reactions and Anaphylaxis*, J. Biol. Chem., 274, 27028 (1999).

D. C. Thomis, et al., *The Jak Family Tyrosine Kinase Jak3 is Required for IL–2 Synthesis by Naïve/Resting CD4+ T Cells*, J. Immunol., 163, 5411 (1999).

E. Chen, et al., *Advances in Cytokine Signaling: The Role of Jaks and STATs*, Transplantation Proc., 31, 1482, (1999).

R. Moriggi, et al., *Stat5 Activation is Uniquely Associated with Cytokine Signaling in Peripheral T Cells*, Immunity, 11, 225 (1995).

L. H. Wang, et al., *JAK3, STAT, and MAPK Signaling Pathways as Novel Molecular Targets for the Tyrphosin AG–490 Regulation of IL–2–Mediated T Cell Response*, J. Immunol., 162, 3897, (1999).

E. A. Sudbeck, et al., *Structure–based Design of Specific Inhibitors of Janus Kinase 3 as Apoptosis–inducing Antileukemic Agents*, Clin. Cancer Res., 5, 1569, (1999).

F. M. Uckun, et al., *In Vivo Toxicity and Pharmacokinetic Features of the Janus Kinase 3 Inhibitor WHI–P131 [40(4'Hydroxyphenyl)–Amino–6,7–Dimethosyquinazolein]*, Clin. Cancer Research, 5, 2954, (1999).

E. A. Sudbeck and F. M. Uckun, *Recent Advances in JAK3 kinase inhibitors*, IDrugs, 2, 1026, (1999).

R. Malaviya, et al., *Genetic and Biochemical Evidence for a Critical Role of Janus Kinase (JAK)–3 in Mast Cell–Mediated Type 1 Hypersensitivity Reactions*, Biochem. Biophys., Res. Commun., 257, 807, (1999).

V. N. Trieu, et al., *A Specific Inhibitor of Janus Kinase–3 Increases Survival in a Transgenic Mouse Model of Amyotrophic Lateral Sclerosis*, Biochem. Biophys. Res. Commun., 267, 22, (2000).

X. C. Li, et al., *Blocking the Common γ–Chain of Cytokine Receptors Induces T Cell Apoptosis and Long–Term Islet Allograft Survival*, J. Immunol., 164, 1193 (2000)/.

R. Malaviya, et al., *Treatment of allergic asthma by targeting Janus kinase 3–dependent leukotriene synthesis in mast cells with 4–(3',5'–Dibromo–4'hydroxyphenyl)amino–6, 7–dimethoxyquinazoline (WHI–P97)*, J. Pharmacol. Exp. Ther., 295, 912 (2000).

S. Ghosh, et al., *4–[(3–Bromo–4–hydroxyphenyl)amino]6, 7–dimethoxyquinazolin–1–ium chloride methanol solvate and 4–(3–hydroxyphenyl)amino0–6, 7–dimethoxy–1–quinazolinium chloride*. Acta Crystallogr., C: Cryst. Struct. Commun., C57, 76 (2001).

E. A. Skudbeck, et. al. *An inhibitor of janus kinase 3: 4–(4–hydroxyphenylamino)–6, 7–dimethoxyquinazolin–1–ium chloride*, Acta Crystallogr., SectC: Cryst. Struct. Commun., C56, 1282 (2000).

\* cited by examiner

MONOCYCLIC-7H-PYRROLO[2,3-D] PYRIMIDINE COMPOUNDS, COMPOSITIONS, AND METHODS OF USE

This application claims the benefit of U.S. provisional application 60/089,886 filed Jun. 19, 1998.

BACKGROUND OF THE INVENTION

The present invention relates to pyrrolo[2,3-d]pyrimidine compounds which are inhibitors of protein tyrosine kinases, such as the enzyme Janus Kinase 3 (hereinafter also referred to as JAK3) and as such are useful therapy as immunosuppressive agents for organ transplants, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

This invention also relates to a method of using such compounds in the treatment of the above indications in mammals, especially humans, and the pharmaceutical compositions useful therefor.

JAK3 is a member of the Janus family of protein tyrosine kinases. Although the other members of this family are expressed by essentially all tissues, JAK3 expression is limited to hematopoetic cells. This is consistent with its essential role in signaling through the receptors for IL-2, IL-4, IL-7, IL-9 and IL-15 by non-covalent association of JAK3 with the gamma chain common to these multichain receptors. XSCID patient populations have been identified with severely reduced levels of JAK3 protein or with genetic defects to the common gamma chain, suggesting that immunosuppression should result from blocking signaling through the JAK3 pathway. Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

SUMMARY OF THE INVENTION

The present invention relates to a compound of the formula

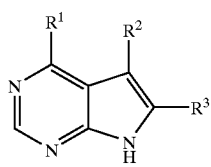

I or the pharmaceutically acceptable salt thereof; wherein
$R^1$ is a group of the formula or when n is at least 1, D and E, or D and X, are each $CR^7R^8$, the adjacent $R^7$ groups may be taken together, with the carbons to which they are attached, to form groups of the formulas

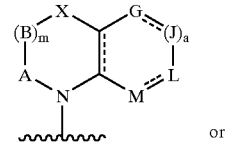

V or

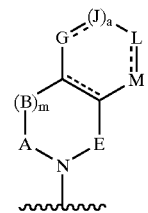

VI wherein the dashed lines represent optional double bonds;
a is 0, 1 or 2;
m, A, B and X are as defined above; and
G, J, L and M are each independently oxygen, $S(O)_d$ wherein d is 0, 1 or 2, $NR^6$ or $CR^7R^8$ wherein $R^6$, $R^7$ and $R^8$ are as defined above;

or when n is 1, D and E are each $CR^7R^8$ and m is 1, A and B are each $CR^7R^8$, the respective adjacent $R^7$ groups may be taken together, with the carbons to which they are attached, to form a group of the formula

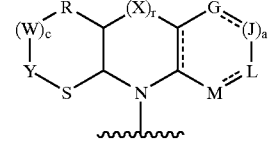

XIII wherein the dashed bond represent optional double bonds;
a, G, J. L and M are as define above;
r is 0 or 1;
c is 0, 1 or 2; and
R, W, Y and S are each independently oxygen, $S(O)_d$ wherein d is 0, 1 or 2, $NR^6$ or $CR^7R^8$ wherein $R^6$, $R^7$ and $R^8$ are as defined above;
$R^2$ and $R^3$ are each independently selected from the group consisting of hydrogen, deuterium, amino, halo, hydoxy, nitro, carboxy, ($C_2$–$C_6$)alkenyl, ($C_2$–$C_6$) alkynyl, trifluoromethyl,

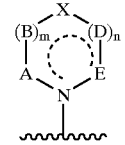

IV wherein the dashed line represents optional double bonds;
m is 0, 1, 2 or 3;
n is 0, 1, 2 or 3;
X, B and D are each independently oxygen, $S(O)_d$ wherein d is 0, 1 or 2, $NR^6$ or $CR^7R^8$;
A and E are each $CR^7R^8$; and
$R^6$ is selected from the group consisting of hydrogen, ($C_1$–$C_6$)alkyl, trifluoromethyl, trifluoromethyl($C_1$–$C_6$)

alkyl, $(C_1-C_6)$alkyl(difluoromethylene), $(C_1-C_3)$alkyl (difluoromethylene)$(C_1-C_3)$alkyl, $(C_1-C_6)$alkoxy $(C_1-C_6)$acyl, $(C_1-C_6)$alkylamino$(C_1-C_6)$acyl, $((C_1-C_6)$alkyl$)_2$amino$(C_1-C_6)$acyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$acyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, hydroxy $(C_2-C_6)$alkyl, $(C_1-C_6)$acyloxy$(C_2-C_6)$alkyl, $(C_1-C_6)$alkoxy$(C_2-C_6)$alkyl, piperazinyl$(C_1-C_6)$alkyl, $(C_1-C_6)$acylamino$(C_1-C_6)$alkyl, $(C_6-C_{10})$aryl$(C_1-C_6)$alkoxy $(C_1-C_6)$alkyl, $(C_5-C_9)$heteroaryl$(C_1-C_6)$alkoxy $(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino$(C_1-C_6)$alkyl, $((C_1-C_6)$alkyl$)_2$amino$(C_1-C_6)$alkyl, $R^{13}CO(C_1-C_6)$alkyl wherein $R^{13}$ is $R^{20}O$ or $R^{20}R^{21}N$ wherein $R^{20}$ and $R^{21}$ are each independently selected from the group consisting of hydrogen, $(C_1-C_6)$alkyl, $(C_6-C_{10})$aryl$(C_1-C_6)$alkyl or $(C_5-C_9)$heteroaryl $(C_1-C_6)$alkyl; or $R^{14}(C_2-C_6)$alkyl wherein $R^{14}$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl, $(C_1-C_6)$alkoxyacyl, $(C_1-C_6)$alkylaminoaryl, $((C_1-C_6)$alkyl$_2$aminoacyl or $(C_1-C_6)$acylpiperidyl;

$R^7$ and $R^8$ are each independently selected from the group consisting of hydrogen, deuterium, $(C_1-C_6)$alkyl, amino, hydroxy, $(C_1-C_6)$alkoxy, $(C_1-C_6)$alkylamino, $((C_1-C_6)$alkyl)amino, $(C_1-C_6)$acylamino, $(C_1-C_6)$acyl $(C_1-C_6)$alkylamino, carboxy, $(C_1-C_6)$alkoxyacyl, $(C_1-C_6)$alkylaminoacyl, $((C_1-C_6)$alkyl$)_2$aminoacyl, aminoacyl, trifluoromethyl, trifluoromethyl$(C_1-C_6)$ alkyl, $(C_1-C_6)$alkyl (difluoromethylene), $(C_1-C_3)$alkyl (difluoromethylene)$(C_1-C_3)$alkyl, $(C_6-C^{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$ aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, hydroxy $(C_1-C_6)$alkyl, $(C_1-C_6)$acyloxy$(C_1-C_6)$alkyl, $(C_1-C_6)$alkoxy$(C_1-C_6)$alkyl, piperazinyl$(C_1-C_6)$alkyl, $(C_1-C_6)$acylamino$(C_1-C_6)$alkyl, piperidyl, $(C_1-C_6)$alkylpiperidyl, $(C_6-C_{10})$aryl$(C_1-C_6)$alkoxy$(C_1-C_6)$alkyl, $(C_5-C_9)$heteroaryl $(C_1-C_6)$alkoxy$(C_1-C_6)$alkyl, $(C_1-C_6)$alkylthio$(C_1-C_6)$alkyl, $(C_6-C_{10})$arylthio $(C_1-C_6)$alkyl, $(C_{1-C_6})$alkylsulfinyl$(C_{1-C_6})$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino $(C_1-C_6)$alkyl, $((C_1-C_6)$alkyl$)_2$amino$(C_1-C_6)$alkyl, $R^{13}CO(C_1-C_6)$alkyl or $R^{13}CO(C_3-C_{10})$cycloalkyl wherein $R^{13}$ is $R^{20}O$ or $R^{20}R^{21}N$ wherein $R^{20}$ and $R^{21}$ are each independently selected from the group consisting of hydrogen, $(C_1-C_6)$alkyl, $(C_6-C_{10})$aryl $(C_1-C_6)$alkyl or $(C_5-C_9)$heteroaryl$(C_1-C_6)$alkyl; $R^{14}$, $R^{14}(C_1-C_6)$alkyl or $R^{14}(C_3-C_{10})$cycloalkyl wherein $R^{14}$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$ heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl or $(C_1-C_6)$acylpiperidyl; or a group of the formula

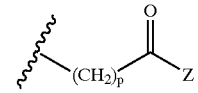

III wherein p is 0, 1, 2 or 3; and

Z is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl, $(C_1-C_6)$acylpiperidyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$ aryl, $(C_6-C_{10})$aryl$(C_6-C_{10})$aryl$(C_1-C_6)$alkyl, $(C_3-C_6)$ cycloalkyl, $(C_3-C_6)$cycloalkyl$(C_1-C_6)$alkyl, $R^5(C_1-C_6)$alkyl, $(C_1-C_5)$alkyl(CHR$^5$)$(C_1-C_6)$alkyl wherein $R^5$ is hydroxy, $(C_1-C_6)$acyloxy, $(C_1-C_6)$ alkoxy, piperazino, $(C_1-C_6)$acylamino, $(C_1-C_6)$ alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$ arylsulfoxyl, amino, $(C_1-C_6)$alkylamino, $((C_1-C_6)$ alkyl$)_2$ amino, $(C_1-C_6)$acylpiperazino, $(C_1-C_6)$ alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^6(C_1-C_6)$alkyl, $(C_1-C_5)$alkyl(CHR$^6$)$(C_1-C_6)$alkyl wherein $R^6$ is piperidyl, $(C_1-C_6)$alkylpiperidyl, $(C_6-C_{10})$arylpiperidyl, $(C_6-C_{10})$aryl$(C_1-C_6)$ alkylpiperidyl, $(C_5-C_9)$heteroarylpiperidyl or $(C_5-C_9)$ heteroaryl$(C_1-C_6)$alkylpiperidyl;

trifluoromethoxy, $(C_1-C_6)$alkyl, $(C_1-C_6)$alkoxy wherein the alkyl or alkoxy groups are optionally substittued by one to three groups selected from halo, hydroxy, carboxy, amino $(C_1-C_6)$alkylthio, $(C_1-C_6)$alkylamino, $((C_1-C_6)$alkyl$)_2$ amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$ arylamino, $(C_1-C_6)$alkylthio, $(C_6-C_{10})$arylthio, $(C_1-C_6)$ alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$ alkyl-CO—NH—, $(C_1-C_6)$alkoxy-CO—NH—, $(C_1-C_6)$ alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$ alkoxy, carboxy, carboxy$(C_1-C_6)$alkyl, carboxy$(C_1-C_6)$ alkoxy, benzyloxycarbonyl$(C_1-C_6)$alkoxy, $(C_1-C_6)$ alkoxycarbonyl$(C_1-C_6)$alkoxy, $(C_6-C_{10})$aryl, amino, amino $(C_1-C_6)$alkyl, $(C_1-C_6)$alkoxycarbonylamino, $(C_6-C_{10})$aryl $(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$ alkoxy, carboxy, carboxy$(C_1-C_6)$alkyl, $(C_1-C_6)$ alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl;

with the proviso that when A, B or X, in formulas V or VI, is defined as $NR^6$ or $CR^7R^8$, $R^2$ and/or $R^3$ must be halo;

with the proviso that when $R^2$ and $R^3$ are each independently hydrogen or $(C_1-C_6)$alkyl, $R^1$ cannot be unsubstituted piperidinyl;

with the proviso that when $R^2$ and $R^3$ are each hydrogen, $R^1$ cannot be unsubstituted mopholinyl or pyrrolidinyl;

with the proviso that when $R^2$ and $R^3$ are each hydrogen, $R^1$ cannot be piperazinyl; and with the proviso that the groups of formulas IV, V, VI or XIII do not contain two or more oxygens, sulfurs or combinations thereof in adjacent positions.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula 1. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (eg, potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The term "alkyl", as used herein, unless otherwise indicated, includes saturated monovalent hydrocarbon radicals having straight, branched or cyclic moieties or combinations thereof.

The term "alkoxy", as used herein, includes 0-alkyl groups wherein "alkyl" is defined above.

The term "halo", as used herein, unless otherwise indicated, includes fluoro, chloro, bromo or iodo.

The compounds of this invention may contain double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (eg, alkoxy), may be linear or branched, and they may also be cyclic (e.g., cyclopropyl, cyclobutyl, cyclopentyl, cyclohexyl or cycloheptyl) or be linear or branched and contain cyclic moieties. Unless otherwise indicated, halogen includes fluorine, chlorine, bromine, and iodine.

$(C_3-C_{10})$Cycloalkyl when used herein refers to cycloalkyl groups containing zero to two levels of unsaturation such as cyclopropyl, cyclobutyl, cyclopentyl, cyclopentenyl, cyclohexyl, cyclohexenyl, 1,3-cyclohexadiene, cycloheptyl, cycloheptenyl, bicyclo[3.2.1]octane, norbornanyl etc.

$(C_2-C_9)$Heterocycloalkyl when used herein refers to pyrrolidinyl, tetrahydrofuranyl, dihydrofuranyl tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-3-yl, tetrahydroazepinyl, piperazinyl, chromanyl, etc. One of ordinary skill in the art will understand that the connection of said $(C_2-C_9)$heterocycloalkyl rings is through a carbon or a sp$^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heteroaryl rings is through a carbon atom or a sp$^3$ hybridized nitrogen heteroatom.

$(C_6-C_{10})$aryl when used herein refers to phenyl or naphthyl.

Compounds of formula (I) may be administered in a pharmaceutically acceptable form either alone or in combination with one or more additional agents which modulate a mammalian immune system or with antiinflammatory agents. These agents may include but are not limited to cyclosporin A (e.g. Sandimmune® or Neoral®, rapamycin, FK-506 (tacrolimus), leflunomide, deoxyspergualin, mycophenolate (e.g. Cellcept®), azathioprine (e.g. Imuran®), daclizumab (e.g. Zenapax®, OKT3 (e.g. Orthoclone®), AtGam, aspirin, acetaminophen, ibuprofen, naproxen, piroxicam, and antiinflammatory steroids (e.g. prednisolone or dexamethasone). These agents may be administered as part of the same or separate dosage forms, via the same or different routes of administration, and on the same or different administration schedules according to standard pharmaceutical practice.

The compounds of this invention include all configurational isomers (es, cis and trans isomers) and all optical isomers of compounds of the formula I (e., enantiomers and diastereomers), as well as racemic, diastereomeric and other mixtures of such isomers. This invention also includes all rotamers of compounds of formula I as well as scelemic mixtures.

Preferred compounds of formula I include those wherein R$^1$ is is a group of the formula $$\text{IV}$$

wherein the dashed line represents optional double bonds;

m is 0, 1, 2 or 3;

n is 0, 1, 2 or 3;

X, B and D are each independently oxygen, S(O)$_d$ wherein d is 0, 1 or 2, NR$^6$ or CR$^7$R$^8$;

A and E are each independently CR$^7$R$^8$ or NR$^6$;

or when n is 1, D and E are each CR$^7$R$^8$ and m is 1, A and B are each CR$^7$R$^8$, the respective adjacent R$^7$ groups may be taken together, with the carbons to which they are attached, to form a group of the formula $$\text{XIII}$$

wherein the dashed bond represent optional double bonds;

a, G, J. L and M are as define above;

r is 0 or 1;

c is 0, 1 or 2; and

R, W, Y and S are each independently oxygen, S(O)$_d$ wherein d is 0, 1 or 2, NR$^6$ or CR$^7$R$^8$ wherein R$^6$, R$^7$ and R$^8$ are as defined above.

Other preferred compounds of formula I include those wherein R$^2$ and R$^3$ are each independently selected from the group consisting of hydrogen, (C$_1$–C$_6$)alkyl, (C$_1$–C$_6$)alkoxy, (C$_3$–C$_{10}$)cycloalkyl, (C$_3$–C$_{10}$)cycloalkoxy, (C$_2$–C$_9$)heterocycloalkyl, (C$_5$–C$_9$)heteroaryl or (C$_6$–C$_{10}$)aryl.

Specific preferred compounds of formula I include the following:

5-Fluoro-4-piperidin-1-yl-7H-pyrrolo[2,3-d]pyrimidine;

4-Piperidin-1-yl-5-trifluoromethyl-7H-pyrrolo[2,3-d]pyrimidine;

2-{3-Ethyl-4-[methyl-(7H-pyrrolo(2,3-d]pyrimidin-4-yl)-aminol-cyclopentyl}-propan-2-ol;

2-{3-Ethyl-4-[(2-hydroxy-ethyl)-(7H-pyrrolo[2,3-d]pyrimidin-4-yl)-amino]-cyclopentyl}-propan-2-ol;

N,N-Dimethyl-N'-[3-(4-piperidin-1-yl-7H-pyrrolo[2,3-d]pyrimidin-5-yl)-benzyl]-ethane-1,2-diamine;

2-[1-(5-m-Tolyl-7H-pyrrolo[2,3-d]pyrimidin-4-yl)-piperidin-4-yl]-ethanol;

5-(3-Isopropyl-phenyl)4-piperidin-1-yl-7H-pyrrolo[2,3-d]pyrimidine;

5-(3-Methyl-3H-imidazol-4-yl)-4-piperidin-1-yl-7H-pyrrolo[2,3-d]pyrimidine;

5-(1-Methyl-1H-imidazol-4-yl)-4-piperidin-1-yl-7H-pyrrolo[2,3-d]pyrimidine;

5-(2-Methyl-pyridin4-yl)-4-piperidin-1-yl-7H-pyrrolo[2,3-d]pyrimidine;

5-Chloro-4-piperidin-1-yl-7H-pyrrolo[2,3-d]pyrimidine;

5-Chloro-4-(octahydro-indol-1-yl)-7H-pyrrolo[2,3-d]pyrimidine;

5-Ethynyl-4-piperidin-1-yl-7H-pyrrolo[2,3-d]pyrimidine;

4-Piperidin-1-yl-5-m-tolyl-7H-pyrrolo[2,3-d]pyrimidine; and 4-(3,3-Dimethyl-piperidin-1-yl)-7H-pyrrolo[2,3-d]pyrimidine.

The present invention also relates to a pharmaceutical composition for (a) treating or preventing a disorder or condition selected from organ transplant rejection, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein tyrosine kinases or Janus Kinase 3 (JAK3) in a mammal, including a human, comprising an amount of a compound of formula I or a pharmaceutically acceptable salt thereof, effective in such disorders or conditions and a pharmaceutically acceptable carrier.

The present invention also relates to a pharmaceutical composition for (a) treating or preventing a disorder or condition selected from organ transplant rejection, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases or (b) the inhibition of protein tyrosine kinases or Janus Kinase 3 (JAK3) in a mammal, including a human, comprising an amount of a compound of formula I or a pharmaceutically acceptable salt thereof, alone or in combination with T-cell immunosuppressant or antiinflammatory agents, effective in such disorders or conditions and a pharmaceutically acceptable carrier.

The present invention also relates to a method for the inhibition of protein typrosine kinases or Janus Kinase 3 (JAK3) in a mammal, including a human, comprising administering to said mammal an effective amount of a compound of formula I or a pharmaceutically acceptable salt thereof.

The present invention also relates to a method for treating or preventing a disorder or condition selected from organ transplant rejection, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of a compound of formula I or a pharmaceutically acceptable salt thereof, effective in treating such a condition.

The present invention also relates to a method for the inhibition of protein typrosine kinases or Janus Kinase 3 (JAK3) in a mammal, including a human, comprising administering to said mammal an effective amount of a compound of formula I or a pharmaceutically acceptable salt thereof, alone or in combination with T-cell immunosuppressant or antiinflammatory agents.

The present invention also relates to a method for treating or preventing a disorder or condition selected from organ transplant rejection, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia, and other autoimmune diseases in a mammal, including a human, comprising administering to said mammal an amount of a compound of formula I or a

DETAILED DESCRIPTION OF THE INVENTION
The following reaction Schemes illustrate the preparation of the cormpounds of the present invention. Unless otherwise indicated $R^1$, $R^2$, $R^3$ and $R^9$ in the reaction Schemes and the discussion that follow are defined as above.
SCHEME 1
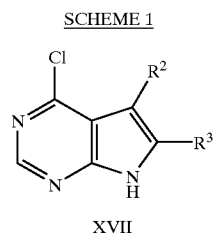
XVII
↓ 1
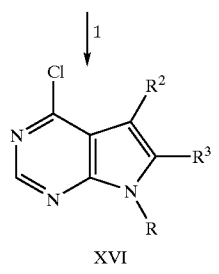
XVI
↓ 2
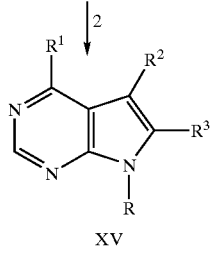
XV
↓ 3
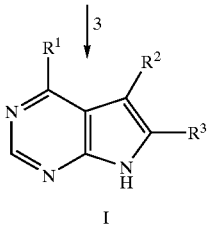
I
SCHEME 2
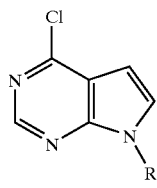
XXI
-continued
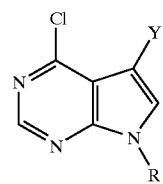
XX
↓ 2
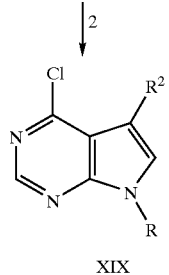
XIX
↓ 3
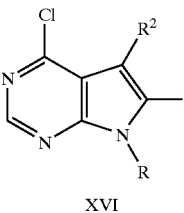
XVI
SCHEME 3
XXI
↓ 1
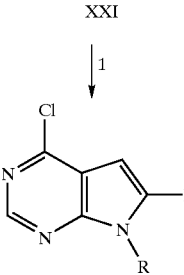
XXII
↓ 2
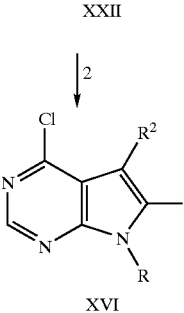
XVI

SCHEME 4

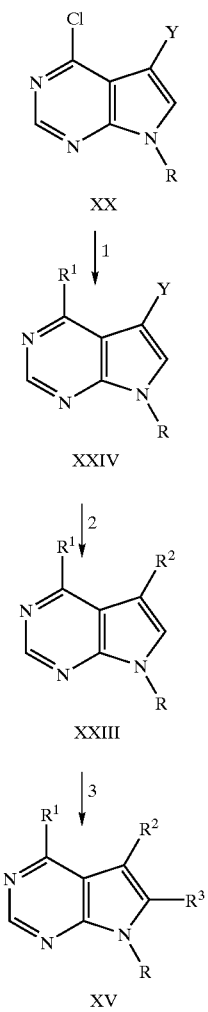

In reaction 1 of Scheme 1, the 4-chloropyrrolo[2,3-d]pyrimidine compound of formula XVII is converted to the corresponding compound of formula XVI, wherein R is benzenesulfonyl or benzyl, by treating XVII with benzenesulfonyl chloride, benzylchloride or benzylbromide in the presence of a base, such as sodium hydride or potassium carbonate, and a polar aprotic solvent, such as dimethylformamide or tetrahydrofuran. The reaction mixture is stirred at a temperature between about 0° C. to about 70° C., preferably about 30° C., for a time period between about 1 hour to about 3 hours, preferably about 2 hours.

In reaction 2 of Scheme 1, the 4-chloropyrrolo[2,3-d]pyrimidine compound of formula XVI is converted to the corresponding 4-aminopyrrolo[2,3-d]pyrimidine compound of formula XV by coupling XVI with a compound of the formula $R^1H$. The reaction is carried out in an alcohol solvent, such as tert-butanol, methanol or ethanol, or other high boiling organic solvents, such as dimethylformamide, 1,4-dioxane or 1,2-dichloroethane, at a temperature between about 60° C. to about 120° C., preferably about 80° C. Typical reaction times are between about 2 hours to about 48 hours, preferably about 16 hours.

In reaction 3 of Scheme 1, removal of the protecting group from the compound of formula XV, wherein R is benzenesulfonyl, to give the corresponding compound of formula I, is carried out by treating XV with an alkali base, such as sodium hydroxide or potassium hydroxide, in an alcohol solvent, such as methanol or ethanol, or mixed solvents, such as alcohol/tetrahydrofuran or alcohol/water. The reaction is carried out at room temperature for a time period between about 15 minutes to about 1 hour, preferably 30 minutes. Removal of the protecting group from the compound of formula XV, wherein R is benzyl, is conducted by treating XV with sodium in ammonia at a temperature of about –78° C. for a time period between about 15 minutes to about 1 hour.

In reaction 1 of Scheme 2, the 4-chloropyrrolo[2,3-d]pyrimidine compound of formula XXI, wherein R is hydrogen or benzenesulfonate, is converted to the 4-chloro-5-halopyrrolo[2,3-d]pyrimidine compound of formula XX, wherein Y is chloro, bromo or iodo, by reacting XXI with N-chlorosuccinimide, N-bromosuccinimide or N-iodosuccinimide. The reaction mixture is heated to reflux, in chloroform, for a time period between about 1 hour to about 3 hours, preferably about 1 hour. Alternatively, in, reaction 1 of Scheme 2, the 4 chloropyrrolo[2,3-d]pyrimidine of formula XXI, wherein R is hydrogen, is converted to the corresponding 4-chloro-5-nitropyrrolo[2,3-d]pyrimidine of formula XX, wherein Y is nitro, by reacting XXI with nitric acid in sulfuric acid at a temperature between about –10° C. to about 10° C., preferably about 0° C., for a time period between about 5 minutes to about 15 minutes, preferably about 10 minutes. The compound of formula XXI, wherein Y is nitro, is converted to the corresponding 4-chloro-5-aminopyrrolo[2,3-d]pyrimidine of the formula XX, wherein Y is amino, by reacting XXI under a variety of conditions known to one skilled in the art such as palladium hydrogenolysis or tin(IV)chloride and hydrochloric acid.

In reaction 2 of Scheme 2, the 4-chloro-5-halopyrrolo[2,3-d]pyrimidine compound of formula XX, wherein R is hydrogen, is converted to the corresponding compound of formula XIX, wherein $R^2$ is $(C_1-C_6)$alkyl or benzyl, by treating XX with N-butyllithium, at a temperature of about –78° C., and reacting the dianion intermediate so formed with an alkylhalide or benzylhalide at a temperature between about –78° C. to room temperature, preferably room temperature. Alternatively, the dianion so formed is reacted with molecular oxygen to form the corresponding 4-chloro-5-hydroxypyrrolo[2,3-d]pyrimidine compound of formula XIX, wherein $R^2$ is hydroxy. The compound of formula XX, wherein Y is bromine or iodine and R is benzenesulfonate, is converted to the compound of formula XIX, wherein $R^2$ is $(C_6-C_{12})$aryl or vinyl, by treating XX with N-butyllithium, at a temperature of about –78° C., followed by the addition of zinc chloride, at a temperature of about –78° C. The corresponding organo zinc intermediate so formed is then reacted with aryliodide or vinyl iodide in the presence of a catalytic quantity of palladium. The reaction mixture is stirred at a temperature between about 50° C. to about 80° C., preferably about 70° C., for a time period between about 1 hour to about 3 hours, preferably about 1 hour.

In reaction 3 of Scheme 2, the compound of formula XIX is converted to the correspondihg compound of formula XVI by treating XIX with N-butyllithium, lithium diisopropylamine or sodium hydride, at a temperature of about –78° C., in the presence of a polar aprotic solvent, such as tetrahydrofuran. The anionic intermediate so formed is further reacted with (a) alkylhalide or benzylhalide, at a temperature between about –78° C. to room temperature, preferably –78° C., when $R^3$ is alkyl or benzyl; (b) an aldehyde or ketone, at a temperature between about –78° C. to room temperature, preferably −78° C., when R³ is alkoxy; and (c) zinc chloride, at a temperature between about −78° C. to room temperature, preferably −78° C., and the corresponding organozinc intermediate so formed is then reacted with aryliodide or vinyl iodide in the presence of a catalytic quantity of palladium. The resulting reaction mixture is stirred at a temperature between about 50° C. to about 80° C., preferably about 70° C., for a time period between about 1 hour to about 3 hours, preferably about 1 hour. Alternatively, the anion so formed is reacted with molecular oxygen to form the corresponding 4-chloro-6-hydroxypyrrolo[2,3-d]pyrimidine compound of formula XVI, wherein R³ is hydroxy.

In reaction 1 of Scheme 3, the 4-chloropyrrolo[2,3-d] pyrimidine compound of formula XXI is converted to the corresponding compound of formula XXII, according to the procedure described above in reaction 3 of Scheme 2.

In reaction 2 of Scheme 3, the compound of formula XXII is converted to the corresponding compound of formula XVI, according to the procedures described above in reactions 1 and 2 of Scheme 3.

In reaction 1 of Scheme 4, the 4-chloropyrrolo[2,3-d] pyrimidine compound of formula XX is converted to the corresponding 4-aminopyrrolo[2,3-d]pyrimidine compound of formula XXIV, according to the procedure described above in reaction 2 of Scheme 1.

In reaction 2 of Scheme 4, the 4-amino-5-halopyrrolo[2, 3-d]pyrimidine compound of formula XXIV, wherein R is benzenesulfonate and Z is bromine or iodine, is converted to the corresponding compound of formula XXIII by reacting XXIV with (a) arylboronic acid, when R² is aryl, in an aprotic solvent, such tetrahydrofuran or dioxane, in the presence of a catalytic quantity. of palladium (0) at a temperature between about 50° C. to about 100° C., preferably about 70° C., for a time period between about 2 hours to about 48 hours, preferably about 12 hours; (b) alkynes, when R² is alkynyl, in the presence of acatalytic quantity of copper (I) iodide and palladium (0), and a polar solvent, such as dimethylformamide, at room temperature, for a time period between about 1 hour to about 5 hours, preferably about 3 hours; and (c) alkenes or styrenes, when R² is vinyl or styrenyl, in the presence of a catalytic quantity of palladiumn in dimethylformamide, dioxane or tetrahydrofuran, at a temperature between about 80° C. to about 100° C., preferably about 100° C., for a time period between about 2 hours to about 48 hours, preferably about 48 hours.

In reaction 3 of Scheme 4, the compound of formula XXIII is converted to the corresponding compound of formula XV, according to the procedure described above in reaction 3 of Scheme 2.

The compounds of the present invention that are basic in nature are capable of forming a wide variety of different salts with various. inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compositions of the present invention may be formulated in a conventional manner using one or more pharmaceutically acceptable carriers. Thus, the active compounds of the invention may be formulated for oral, buccal, intranasal, parenteral (eg, intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., asthma) is 0.1 to 1000 mg of the active ingredient per unit dose which could be administered, for example, 1 to 4 times per day.

Aerosol formulations for treatment of the conditions referred to above (es, rheumatoid arthritis) in the average adult human are preferably arranged so that each metered dose or "puff" of aerosol contains 20 $\mu$g to 1000 $\mu$g of the compound of the invention. The overall daily dose with an aerosol will be within the range 0.1 mg to 1000 mg. Administration may be several times daily, for example 2, 3, 4 or 8 times, giving for example, 1, 2 or 3 doses each time.

A compound of formula (I) administered in a pharmaceutically acceptable form either alone or in combination with one or more additional agents which modulate a mammlian immune system or with antiinflammatory agents, agents which may include but are not limited to cyclosporin A (e.g. Sandimmunec® or Neoral®, rapamycin, FK-506 (tacrolimus), leflunomide, deoxyspergualin, mycophenolate (e.g. Cellcept®), azathioprine (e.g. Imuran®), daclizumab (e.g. Zenapax®), OKT3 (e.g. Orthocolone®), AtGam, aspirin, acctaminophen, ibuprofen, naproxen, piroxicam, and antiinflmmatory steroids (e.g. prednisolone or dexamethasone); and such agents may be administered as part of the same or separate dosage forms, via the same or different routes of administration, and on the same or different administration schedules according to standard pharmaceutical practice.

FK506 (Tacrolimus) is given orally at 0.10–0.15 mg/kg body weight, every 12 hours, within first 48 hours postoperative. Does is monitored by serum Tacrolimus trough levels. Cyclosporin A (Sandimmune oral or intravenous formulation, or Neoral®, oral solution or capsules) is given orally at 5 mg/kg body weight, every 12 hours within 48 hours postoperative. Dose is monitored by. blood Cyclosporin A trough levels.

The active agents can be formulated for sustained delivery according to methods well known to those of ordinary skill in the art. Examples of such formulations can be found in U.S. Pat. Nos. 3,538,214, 4,060,598, 4,173,626, 3,119,742, and 3,492,397.

The ability of the compounds of formula I or their pharmaceutically acceptable salts to inhibit Janus Kinase 3 and, consequently, demonstrate their effectiveness for treating disorders or conditions characterized by Janus Kinase 3 is shown by the following in vitro assay tests.

Biological Assay
JAK3 (JH1:GST) Enzymatic Assay

The JAK3 kinase assay utilizes a protein expressed in baculovirus-infected SF9 cells (a fusion protein of GST and the catalytic domain of human JAK3) purified by affinity chromatography on glutathione-Sepaharose. The substrate for the reaction is poly-Glutamic acid-Tyrosine (PGT (4:1), Sigma catalog #P0275), coated onto Nunc Maxi Sorp plates at 100 $\mu$/ml overnight at 37° C. The morning after coating, the plates are washed three times and JAK3 is added to the wells containing 100 $\mu$l of kinase buffer (50 mM HEPES, pH 7.3, 125 mM NaCl, 24 mM MgCl2)+0.2 uM ATP+1 mM Na orthovanadate.) The reaction proceeds for 30 minutes at room temperature and the plates is washed three more times. The level of phosphorylated tyrosine in a given well is quantitated by standard ELISA assay utilizing an anti-phosphotyrosine antibody (ICN PY20, cat. #69-151-1).

DND 39/IL-4 Cellular Assay for JAK3 kinase Inhibitors

The DND 39/IL-4 assay is designed to find inhibitors of JAK3 kinase activity which would be prime candidates for immunosupressive and/or allergy. The assay uses a B-cell line called DND39 which has had the luciferase gene driven by the germ line IgE promoter stably integrated into one of the chromosomes. When these cells are stimulated with IL-4, the kinase JAK3, which is associated with the IL-4 receptor, phosphorylates the signal transducer STAT6. STAT6 then blinds to the germline IgE promoter and starts transcription of the luciferase gene. Luciferase is measured in a lysate of these cells using the Promega luciferase assay reagent system.

Note: DND39 cells are grown in RPMI 1640 supplemented with 10% heat inactivated FCS, 2 mM L-Glutamine, and 100 units/ml Pen./Strep. The cells are maintained from $1\times10^5$ to $1\times10^6$ cells/ml. Split to $1\times10^5$ on Friday, cells will be at about $1\times10^6$ on Monday. Then split 1:2 during the week keeping 200 ml in a flask as needed.

$3\times10^5$ DND39 cells are plated in 100 $\mu$l of RPMI 1640 supplemented with 1% heat inactivated FCS, 2 mM L-glutamine, and 100 units/ml Pen/Step in a 96 well Vee bottom plate (Nunc). Compounds are diluted serially 1:2 in DMSO starting at 4 mM to 1.9 $\mu$M. In a 96 well polypropylene plate, changing tips after each dilution. Then 5 $\mu$l of each dilution are added to 500 $\mu$l of RPMI/1% serum in a 96 tube rack. 125 $\mu$L of the compound dilutions are added to the cells and incubated at 37° C., 5% $CO_2$ for one hour. After one hour, 25 $\mu$l of 25 ng/ml IL-4 is added to the cells and mixed. Final concentration of IL-4 is 2.5 ng/ml and final concentration of compound is from 20 $\mu$M to 156 nM. The cells are then incubated overnight 16–18 hours. The plate is then centrifuged at 2500–3000 RPM in a table top centrifuge for 5 minutes. The culture supernatant is carefully removed by aspiration with an 8 well maifold. 100 $\mu$l of PBS with calcium and magnesium is added to the pelletted cells. The cells are resuspended in the PBS and transferred to a Packard white OptiPlate. 100 $\mu$l of Packard's LucLite reagent is added to the wells of the OptiPlate.

The following Examples illustrate the preparation of the compounds of the present invention but it is not limited to the details thereof. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20–25° C.

EXAMPLE 1

Cyclohexyl-methyl-(7H-pyrrolo[2,3-d]pyrimidin-4-yl)-amine

Method A

Cyclohexyl-methyl-(7H-pyrrolo[2,3-d]pyrimidin-4-yl)-amine

A mixture of 200 mg (1.30 mmol) of 4-chloro-7H-pyrrolo[2,3-d]pyrimidine (prepared by the method of Davoll, J. Am. Chem. Soc., (1960), 82, 131), the product from Method A (589 mg/5.21 mmol) and 3 mL of tert-butanol was stirred in a sealed tube at 100° C. for 24 hours. The reaction mixture was added to water, acidified to pH 1 with 1 N hydrochloric acid (aq), washed twice with diethylether (ether) and basified to pH 14 with 1 N sodium hydroxide (NaOH). The resulting precipitate was filtered and dried in vacuo to obtain 263 mg (88%) of the title compound, mp 177–180° C. $^1$H NMR (400 MHz, CDCl$_3$): δ1.11–1.22 (m, 1H), 1.43–1.63 (m, 4H), 1.73 (br d, 1H, J=13.3 Hz), 1.83–1.90 (m, 4 H), 3.23 (s, 3H), 4.69 (br, 1H), 6.53 (d, 1H, J=3.5 Hz), 7.03 (d, 1H, J=3.5 Hz), 8.30 (s, 1H), 10.6 (br, 1H). LRMS: 231 (M+1).

The title compounds of Examples 2–51 were prepared by a method analogous to that described in Example 1.

EXAMPLE 2

9-(7H-Pyrrolo[2,3-d]pyrimidin-4-yl)-2,3,4,4a,9,9a-hexahydro-1H-carbazole

EXAMPLE 3

4-(2,6-Dimethyl-morpholin-4-yl)-7H-pyrrolo[2,3-d]pyrimidine 2,6-Dimethylmorpholine. LRMS: 233.3.

EXAMPLE 4

4-Morpholin-4-yl-7H-pyrrolo[2,3-d]pyrimidine

4-Morpholine. LRMS: 205.

EXAMPLE 5

4-(2,5-Dimethyl-pyrrolidin-1-yl)-7H-pyrrolo[2,3-d]pyrimidine 2,5-Dimethylpyrrolidine. Melting Point: 227–229° C.; LRMS: 216.3.

EXAMPLE 6

4-(4-Benzyl-piperidin-1-yl)-7H-pyrrolo[2,3-d]pyrimidine

4-Benzylpiperidine. Melting Point: 188–190° C.; LRMS: 292.4.

EXAMPLE 7

4-Phenyl-1-(7H-pyrrolo[2,3-d]pyrimidin-4-yl)-piperidin-4-ol

4-Phenylpiperidin-4-ol. Melting Point: 201–202° C.; LRMS: 294.4.

EXAMPLE 8

1-[1-(7H-Pyrrolo[2,3-d]pyrimidin-4-yl)-piperidin-4-yl]-1,3-dihydro-benzoimidazol-2-one Piperidin-4-yl-1,3-dihydrobenzoimidazole. Melting Point: 182–184° C.; LRMS: 334.4.

EXAMPLE 9

1-Phenyl-8-(7H-pyrrolo[2,3-d]pyrimidin4-yl)-1,3,8-triaza-spiro[4.5]decan4-one

1-Phenyl-1,3,8-triaza-spiro[4.5]decan-4-one. Melting Point: 232–234° C.

EXAMPLE 10

4-(3-Methyl-piperidin-1-yl)-7H-pyrrolo[2,3-d]pyrimidine

3-Methylpiperidine. Melting Point: 176–178° C.; LRMS: 217.1.

EXAMPLE 11

4-(3,5-Dimethyl-piperidin-1-yl)-7H-pyrrolo[2,3-d]pyrimidine 3,5-Dimethylpiperidine. Melting Point: 258–260° C.; LRMS: 231.

EXAMPLE 12

4-(2-Methyl-piperidin-1-yl)-7H-pyrrolo[2,3-d]pyrimidine

2-Methyl-piperidine. Melting Point: 144–146° C.; LRMS: 217.1.

EXAMPLE 13

4-(2-Ethyl-piperidin-1-yl)-7H-pyrrolo[2,3-d]pyrimidine

2-Ethylpiperidine. Melting Point: 112–114° C.; LRMS: 231.

EXAMPLE 14

[1-(7H-Pyrrolo[2,3-d]pyrimidin 4-yl)-piperidin-2-yl]-methanol

Piperidine-2-yl-methanol. Melting Point: 135–136° C.; LRMS: 232.9.

EXAMPLE 15

1-(7H-Pyrrolo[2,3-d]pyrimidin4-yl)-piperidine-3-carboxylic acid diethylamide

Piperidine-3-carboxylic acid diethylamide. LRMS: 302.1.

EXAMPLE 16

2-[1-(7H-Pyrrolo[2,3-d]pyrimidin-4-yl)-piperidin-2-yl]-ethanol

Piperidin-2-yl-ethanol. Melting Point: 139–140° C.

EXAMPLE 17

4-Azocan-1-yl-7H-pyrrolo[2,3-d]pyrimidine

Azapane. Melting Point: 225–226° C.; LRMS: 231.3.

EXAMPLE 18

1-(7H-Pyrrolo[2,3-d]pyrimidin4-yl)-piperidine-3-carboxylic acid amide

Piperidine-3-carboxylic acid amide. Melting Point: 283–285° C.

EXAMPLE 19

Dimethyl-[1-(7H-pyrrolo[2,3-d]pyrimidin-4-yl)-pyrrolidin-3-yl]-amine

Dimethylpyrrolidin-3-yl-amine. Melting Point: 210–212° C.; LRMS: 232.2.

EXAMPLE 20

N-Ethyl-N-[1-(7H-pyrrolo[2,3-d]pyrimidin-4-yl)-pyrrolidin-3-yl]-acetamide

N-Ethylpyrrolidin-3-yl-acetamide. Melting Point: 197–199° C.; LRMS: 274.3.

EXAMPLE 21

4-(2-Methoxymethyl-pyrrolidin-1-yl)-7H-pyrrolo[2,3-d]pyrimidine

2-Methoxymethylpyrrolidine. Melting Point: 134–135° C.; LRMS: 233.2.

EXAMPLE 22

[1-(7H-Pyrrolo[2,3-d]pyrimidin-4-yl)-pyrrolidin-2-yl]-methanol

Pyrrolidin-2-yl-methanol. Melting Point: 188–189° C.; LRMS: 219.3.

EXAMPLE 23

N-[1-(7H-Pyrrolo[2,3-d]pyrimidin-4-yl)-pyrrolidin-3-yl]-acetamide

Pyrrolidin-3-yl-acetamide. Melting Point: 260–261° C.; LRMS: 246.3.

EXAMPLE 24

4-(2-Propyl-piperidin-1-yl)-7H-pyrrolo[2,3-d]pyrimidine

Propylpiperidine. Melting Point: 106–107° C.; LRMS: 245.3.

EXAMPLE 25

4-(4-Methyl-piperazin-1-yl)-7H-pyrrolo[2,3-d]pyrimidine

4-Methylpiperazine. Melting Point: 141–142° C.

EXAMPLE 26

4-Piperazin-1yl-7H-pyrrolo[2,3-d]pyrimidine

Piperazine. Melting Point: 164–166° C.

EXAMPLE 27

4-Azepan-1-yl-7H-pyrrolo[2,3-d]pyrimidine

Azapane. Melting Point: 210° C.; LRMS: 217.3.

EXAMPLE 28

1-(7H-Pyrrolo[2,3-d]pyrimidin-4-yl)-pyrrolidin-3-ol

Pyrrolidin-3-ol. Melting Point: 220–225° C.; LRMS: 205.2.

EXAMPLE 29

[1-(7H-Pyrrolo[2,3-d]pyrimidin-4-yl)-piperidin-3-yl]-methanol

Piperidine-3-yl-methanol. Melting Point: 161.5–163.5° C.; LRMS: 234.3.

EXAMPLE 30

1-(7H-Pyrrolo[2,3-d]pyrimidin4-yl)-piperidine-4-carboxylic acid ethyl ester

Piperidine4-carboxylic acid ethyl ester. Melting Point: 139–141° C.; LRMS: 275.3.

EXAMPLE 31

1-(7H-Pyrrolo[2,3-d]pyrimidin4-yl)-piperidine-3-carboxylic acid ethyl ester

Piperidine-3-carboxylic acid ethylester. Melting Point: 139.5–141.5° C.; LRMS: 275.3.

EXAMPLE 32

2-[1-(7H-Pyrrolo[2,3-d]pyrimidin-4-yl)-piperidin-4-yl]-ethanol

Piperidin-4-yl-ethanol. Melting Point: 129–131° C.; LRMS: 265.3.

EXAMPLE 33

4-(4-Phenyl-piperidin-1-yl)-7H-pyrrolo[2,3-d]pyrimidine

4-Phenylpiperidine. Melting Point: 195° C.; LRMS: 279.

EXAMPLE 34

4-(4-Trifluoromethyl-piperidin-1-yl)-7H-pyrrolo[2,3-d]pyrimidine

4-Trifluoromethylpiperidine. Melting Point: 198° C.; LRMS: 271.

EXAMPLE 35

4-[4-(3-Phenyl-propyl)-piperidin-1-yl]-7H-pyrrolo[2,3-d]pyrimidine 4-(3-Phenylpropyl)piperidine. Melting Point: 134° C.; LRMS: 321.

EXAMPLE 36

4-(3,3-Dimethyl-piperidin-1-yl)-7H-pyrrolo[2,3-d]pyrimidine 3,3-Dimethylpiperidine. Melting Point: 204° C.; LRMS: 231.

EXAMPLE 37

1-(7H-Pyrrolo[2,3-d]pyrimidin-4-yl)-piperidine-3-carboxylic acid

Piperidine-3-carboxylic acid. Melting Point: 159–160° C.; LRMS: 307.3.

EXAMPLE 38

1-Methyl-10-oxa-4-aza-tricyclo[5.2.1.0%2,6&]decane

1-Methyl-4-(7H-pyrrolo[2,3-d]pyrimidin-4-yl)-10-oxa-4-aza-tricyclo[5.2.1]decane. Melting Point: 251–252° C.; LRMS: 271.3.

EXAMPLE 39

1-(5-Chloro-7H-pyrrolo[2,3-d]pyrimidin-4-yl)-decahydroquinoline

Decahydro-quinoline. Melting Point: 190–192° C.; LRMS: 291.8.

EXAMPLE 40

3-[1-(7H-Pyrrolo[2,3-d]pyrimidin-4-yl)-piperidin-3-yl]-propionic acid ethyl ester Piperidin-3-yl-propionic acid ethyl ester. Melting Point: 101–103° C.; LRMS: 303.4.

EXAMPLE 41

3-[1-(7H-Pyrrolo[2,3-d]pyrimidinn-4-yl)-piperidin-3-yl]-propionic acid

Piperidine-3-yl-propionic acid. Melting Point: 217–219° C.; LRMS: 275.3.

EXAMPLE 42

1-(7H-Pyrrolo[2,3-d]pyrimidin4-yl)-piperidin-3-ol

Piperidin-3-ol. Melting Point: 152–154° C.; LRMS: 219.3.

EXAMPLE 43

3-[1-(7H-Pyrrolo[2,3-d]pyrimidin-4-yl)-piperidin-3-yl]-propionamide

Piperidin-3-yl-propionamide. Melting Point: 212–214° C.; LRMS: 274.3.

EXAMPLE 44

4-(2,6-Dimethyl-piperidin-1-yl)-7H-pyrrolo[2,3-d]pyrimidine 2,6-Dimethylpiperidine. LRMS: 231.

EXAMPLE 45

2-[1-(7H-Pyrrolo[2,3-d]pyrimidin4-yl)-piperidin-3-yl]-propan-2-ol

Piperidin-3-yl-propan-2-ol. Melting Point: 182.8–183.6° C.; LRMS: 261.

EXAMPLE 46

2-[1-(7H-Pyrrolo[2,3-d]pyrimidin4-yl)-piperidin-4-yl]-propan-2-ol

Piperidin-4-yl-propan-2-ol. Melting Point: 170.1–171.3° C.; LRMS: 261.

EXAMPLE 47

4-Methyl-1-(7H-pyrrolo[2,3-d]pyrimidin-4-yl)-piperidin-4-ol

4-Methylpiperdin4-ol. Melting Point: 163.8–165.1° C.; LRMS: 233.1.

EXAMPLE 48

3-Methyl-8-(7H-pyrrolo[2,3-d]pyrimidin-4-yl)-8-aza-bicyclo[3.2.1]octan-3-ol

3-Methyl-8-aza-bicyclo[3.2.1]octan-3-ol. Melting Point: 142.1–143.8° C.; LRMS: 259.1.

EXAMPLE 49

2-[1-(7H-Pyrrolo[2,3-d]pyrimidin4-yl)-pyrrolidin-2-yl]-propan-2-ol

Pyrrolidin-2-yl-propan-2-ol. Melting Point: 173 dec; LRMS: 247.1.

EXAMPLE 50

3-Methyl-1-(7H-pyrrolo[2,3-d]pyrimidin-4-yl)-pyrrolidin-3-ol

3-Methylpyrrolidin-3-ol. LRMS: 219.

EXAMPLE 51

4-Pyrazol-1-yl-7H-pyrrolo[2,3-d]pyrimidine

Pyrazole. LRMS: 186.2.

EXAMPLE 52

Cyclohexyl-methyl-(6-phenyl-7H-pyrrolo[2,3-d]pyrimidin-4-yl)-amine

Cyclohexylmethylamine.

METHOD B

7-Benzenesulfonyl-4-chloro-7H-pyrrolo[2,3-d]pyrimidine

In a flame-dried flask under nitrogen, 780 mg of 60% sodium hydride (19.5 mmol) in mineral oil was added to 30 mL of dimethylformamide (DMF) and the resulting mixture cooled to 0° C. A solution of 2.0 g (13.0 mmol) of 4-chloro-7H-pyrrolo[2,3-d]pyrimidine in 10 mL of DMF was added slowly over a 5 minute period. The reaction was stirred for 10 min at which time generation of hydrogen ($H_2$) ceased. Benzenesulfonylchloride (1.7 mL/13.0 mmol) was added, the reaction warmed to room temperature and stirred for 1 hour. Water was added, and the resulting precipitate was filtered and dried in vacuo to obtain 3.4 grams (89%) of the title compound as a crystalline solid, mp 163–167° C.

METHOD C

7-Benzenesulfonyl4-chloro-6-phenyl-7H-pyrrolo[2,3-d]pyrimidine

In a flame-dried flask under nitrogen, 0.53 mL (3.79 mmol) of diisopropylamine were dissolved in 5 mL of tetrahydrofuran (THF) and the solution cooled to −78° C. n-Butyllithium (3.75 mmol as a 2.5 M solution in hexanes) was added and the resulting mixture brought to 0° C. with continued stirring for 10 minutes. The reaction mixture was again cooled to −78° C. and to this mixture added a solution of 1.0 grams (3.40 mmol) of the product from Method B in 10 mL of THF over a 10 min period. The reaction mixture was stirred for 1 hour at −78° C., at which time, 8.2 mL (4.10 mmol) of a 0.5 M solution of zinc chloride in THF was added, the reaction mixture was brought to room temperature and stirred for 1 hour. Iodobenzene (0.46 mL/4.11 mmol) and a suspension of 197 mg of tetrakis(triphenylphosphine) palladium in 2 mL of THF were added. The resulting mixture was stirred at reflux for 3 hours, cooled to room temperature, and partitioned between dichloromethane and water. The aqueous layer was acidified with 1 N HCl and extracted twice with dichloromethane. The dichloromethane layers were combined, washed with 1 N HCl and brine, dried over magnesium sulfate ($MgSO_4$), filtered and concentrated in vacuo to obtain the title compound. LRMS: 370, 372 (M+2).

METHOD D

4-Chloro-6-phenyl-7H-pyrrolo[2,3-d]pyrimidine

The product from Method C was dissolved in 10 mL of THF and to this solution was added 5.0 mL of methanol and 1.0 grams of NaOH. The reaction mixture was stirred for 15 minutes, concentrated in vacuo and partitioned between a saturated aqueous solution of ammonium chloride ($NH_4Cl$) and ethyl acetate. The resulting aqueous layer was extracted twice with ethyl acetate. The ethylacetate layers were combined, washed with brine, dried over $MgSO_4$, filtered and concentrated in vacuo. The crude product was purified by silica-gel chromatography (1:5 ethyl-acetate/hexane) to obtain 0.59 grams (76%) of the title compound as a pale yellow solid, mp 145° C. (dec). LRMS: 230, 232 (M+2).

METHOD E

Cyclohexyl-methyl-(6-phenyl-7H-pyrrolo[2,3-d]pyrimidin-4-yl)-amine

The product from Method D (50 mg/0.218 mmol) was reacted with 0.12 mL of N-methylcyclohexylamine (0.920 mmol) as described in Method A. The reaction mixture was concentrate in vacuo, methanol was added, and the resulting precipitate filtered to provide 7 mg (10%) of the title compound as a yellow solid $^1H$ NMR (400 MHz, $CDCl_3$)δ: 1.18–1.25 (m, 1H), 1.47–1.66 (m, 4H), 1.75–1.90 (m, 5H), 3.30 (s, 3H), 4.74 (br, 1H), 6.79 (s, 1H), 7.32–7.36 (m, 1H), 7.47–7.51 (m, 2H), 7.77 (d, 2H, J=7.9 Hz), 8.33 (s, 1H). LRMS: 307 (M+1).

The title compounds of Examples 53–58 were prepared by a method analogous to that described in Example 52.

EXAMPLE 53

1-(6-Phenyl-7H-pyrrolo[2,3-d]pyrimidin-4-yl)-decahydro-quinoline

Decahydroquinoline. LRMS: 333.4.

EXAMPLE 54

4-(2-Ethyl-piperidin-1-yl)-6-phenyl-7H-pyrrolo[2,3-d]pyrimidine

2-Ethylpiperidine. LRMS: 307.4.

EXAMPLE 55

4-(3,3-Dimethyl-piperidin-1-yl)-6-phenyl-7H-pyrrolo[2,3-d]pyrimidine 3,3-Dimethylpiperidine. LRMS: 307.4.

EXAMPLE 56

6-Phenyl-4-piperidin-1-yl-7H-pyrrolo[2,3-d]pyrimidine

Piperidine. LRMS: 279.4.

EXAMPLE 57

4-Piperidin-1-yl-6-thiophen-3-yl-7H-pyrrolo[2,3-d]pyrimidine

Piperidine. LRMS: 285.4.

EXAMPLE 58

4-Piperidin-1-yl-6-thiophen-2-yl-7H-pyrrolo[2,3-d]pyrimidine

Piperidine. LRMS: 285.4.

EXAMPLE 59

Cyclohexyl-methyl-(6-methyl-7H-pyrrolo[2,3-d]pyrimidin-4-yl)-amine

Cyclohexylmethylamine.

METHOD F

7-Benzenesulfonyl-4-chloro-6-methyl-7H-pyrrolo[2,3-d]pyrimidine

To flame-dried flask under $N_2$ was charged 0.57 ml (4.07 mmol) of diisopropylamine and 5.0 mL of dry THF. The solution was cooled to −78 OC and 1.63 mL (4.08 mmol) of a 2.5 M solution of n-butyllithium in hexanes added. The resulting mixture was brought to 0° C. and stirred for 10 minutes. After cooling the mixture again to −78° C., a solution of 1.0 g (3.40 mmol) of crude product from Method C in 10 mL of dry THF was added over a 10 minute period. The resulting mixture was stirred for 1 hour, at which time, 0.28 mL (4.50 mmol) of iodomethane were added. The reaction mixture was stirred for 2 hours, quenched with a saturated solution of $NH_4Cl$ and warmed to room temperature. The mixture was stirred for 5 minutes, diluted with water and extracted three times with ethyl acetate. The combined extracts were washed with brine, dried over $MgSO_4$, filtered and evaporated in vacuo to obtain the title compound. LRMS: 308, 310 (M+2).

METHOD G

4-Chloro-6-methyl-7H-pyrrolo[2,3-d]pyrimidine

The product from Method F was deprotected as described in Method E. The crude product was purified by trituration with hexanes and dichloromethane to obtain 250 mg (44%) of the title compound as a yellow solid. Mp 205° C. dec. LRMS 168, 170 (M+2).

METHOD H

Cyclohexyl-methyl-(6-methyl-7H-pyrrolo[2,3-d]pyrimidin-4-yl)-amine

The product from Method G (50 mg/0.298 mmol) was reacted with 100 mg (0.883 mmol) of N-methylcyclohexylamine as described in Method A. The reaction mixture was worked up as in Method A with the exception that ethyl acetate was used in place of ether. The title compound (42 mg, 58% yield) was obtained as a white solid. Mp 221° C. dec. $^1$H NMR (400 MHz, CDCl$_3$)δ: 1.15–1.25 (m, 1H), 1.43–1.62 (m, 4H), 1.73 (br s, 1H, J=13.7 Hz), 1.82–1.90 (m, 4H), 2.41 (d, 3H, J=0.8 Hz), 3.21 (s, 3H) 4.63 (br s, 1H), 6.20 (s, 1H), 8.22 (s, 1H), 10.1 (br s, 1H). LRMS: 245 (M+1).

The title compound of Example 60 was prepared by a method analogous to that described in Example 59.

EXAMPLE 60

6-Methyl-4-piperidin-1-yl-7H-pyrrolo[2,3-d] pyrimidine

Piperidine. LRMS: 217.3.

EXAMPLE 61

5-Chloro-4-piperidin-1-yl-7H-pyrrolo[2,3-d] pyrimidine

METHOD I 4,5-Dichloro-7H-pyrrolo[2,3-d]pyrimidine

4-Chloro-7H-pyrrolo[2,3-d]pyrimidine (154 mg, 1.0 mmol) was suspended in 6.0 mL of dry dichloromethane in a flame-dried flask and to this mixture was added N-chlorosuccinimide (147 mg, 1.1 mmol) in one portion. The resulting mixture stirred at room temperature for 18 h, at which time the solvent was removed under reduced pressure. The residue was triturated with water and isolated by filtration to afford 137 mg (72%) of the title compound as a gray solid, mp 224–227° C.(dec). LRMS: 188 (M+1).

METHOD J

5-Chloro-4-piperidin-1-yl-7H-pyrrolo[2,3-d] pyrimidine

The product from Method I (57 mg, 0.3 mmol) was suspended in 3:0 mL of tert-butanol and to this solution was added piperidine (90 μL, 0.9 mmol) and the resulting system heated at reflux for 1 hour. The reaction mixture was cooled to room temperature and water was added (4.0 mL). The solution was adjusted to pH 1 with 1 N HCl and then washed with ether. The aqueous layer was removed and adjusted to pH 12 with 2 N NaOH. The solution was then extracted 2×15 mL with dichloromethane and the combined organics washed with water then brine and dried over MgSO$_4$. Evaporation of solvent afforded 45 mg of a yellow solid that was purified by silica-gel chromatography (3:1 ethyl acetate/hexanes) to yield 23 mg (32%) of the title compound as a light yellow solid. Mp 170–172° C. $^1$H NMR (400 MHz, CDCl$_3$)δ: 1.67–1.74 (m, 6H), 3.65–3.67 (m, 4H), 7.10 (s, 1H), 8.31 (s, 1H), LRMS: 237 (M+1).

The title compounds of Examples 62–63 were prepared by a method analogous to that described in Example 61.

EXAMPLE 62

5-Chloro4-(octahydro-indol-1-yl)-7H-pyrrolo[2,3-d] pyrimidine

Octahydroindole. Melting Point: 193° C.; LRMS: 277.8.

EXAMPLE 63

1-(5-Chloro-7H-pyrrolo[2,3-d]pyrimidin4-yl)-decahydro-quinoline

Decahydroquinoline. Melting Point: 190–192° C.; LRMS: 291.8.

EXAMPLE 64

5-Phenyl-4-piperidin-1-yl-7H-pyrrolo[2,3-d] pyrimidine

METHOD K

5-Bromo-4-chloro-7H-pyrrolo[2,3-d]pyrimidine

To a stirred solution of 4-chloro-7H-pyrrolo[2,3-d] pyrimidine (30 g/0.02 mol) dissolved in 75 mL of chloroform was added 3.5 grams (0.02 mol) of N-bromosuccinamide and the resulting mixture refluxed for 1 hour. After cooling to room temperature, the precipitate was removed by filtration and dried under reduced pressure affording 4.1 grams (89%) of the title compound. $^1$H NMR (400 MHz) (CDCl$_3$)δ: 7.93 (d, 1H, J=2.8 Hz), 8.60 (s, 1H).

METHOD L

7-Benzenesulfonyl-5-bromo-4-chloro-7H-pyrrolo[2,3-d]pyrimidine

To a slurry of the product from Method K (4.1 g/0.018 mol) in DMF (15 mL) and cooled to 0° C. was added 1.0 g (0.025 mol) of 60% sodium hydride in mineral oil and the resulting mixture stirred at 0° C. for 15 minutes. Benzenesulfonyl chloride (3.2 g/0.018 mol) was added, the reaction mixture warmed to room temperature and stirred for 2 hours. Water was then added (15 mL) and the resulting solid removed by filtration and dried in vacuo affording 5.9 grams (89%) of the title compound.

METHOD M

7-Benzenesulfonyl-5-bromo-4-piperidin-1-yl-7H-pyrrolo[2,3-d]pyrimidine

A mixture of 2.0 g (5.37 mmol) of the product from Method L and 1.1 grams (13.4 mmol) of piperidine in 10 mL of tert-butanol was heated with stirring at 60° C. for 2 hours. After cooling to room temperature, the reaction mixture was partitioned between dichloromethane (25 mL) and water (25 mL). The dichloromethane layer was dried over sodium sulfate (Na$_2$SO$_4$) and concentrated to dryness in vacuo affording 2.2 grams (97%) of the title compound. $^1$H NMR (400 MHz) (CDCl$_3$)δ: 1.63–1.72 (m, 6H), 3.54–3.57 (m, 4H), 7.53 (t, 2H, J=2.0 Hz), 7.60 (s, 1H), 7.61 (t, 1H, J=2.0 Hz), 8.17–8.20 (m, 2H), 8.43 (s, 1H). LRMS: 422.7, 420.7 (M+1).

METHOD N

5-Phenyl-4-piperidin-1-yl-7H-pyrrolo[2,3-d] pyrimidine

To a stirred solution of the product from Method M (100 mg/0.237 mmol) in 1.0 mL of dioxane was added 32 mg (0.261 mmol) of phenylboronic acid and 75 mg (0.356 mmol) of tribasic potassium phosphate followed by 7 mg (0.006 mmol) of tetrakis(triphenylphosphine) palladium. The resulting mixture was degassed with nitrogen and stirred at 100° C. for 48 hours. After cooling to room temperature, 1.0 mL of methanol was added followed by 50 mg of NaOH and the new mixture stirred at room temperature for 1 hour. The resulting mixture was then partitioned between dichloromethane and water, the dichloromethane layer dried over MgSO$_4$ and concentrated to dryness in vacuo. The crude product was purified by silica-gel chromatography (2:1 ethyl acetate/hexanes) affording 13 mg (20%) of the title compound. $^1$H NMR (400 MHz) (CDCl$_3$) δ: 1.33–1.34 (m, 4H), 1.43–1.44 (m, 2H), 3.26–3.28 (m, 4H), 7.12 (s, 1H), 7.27 (t, 1H, J=7.2 Hz), 7.38 (t, 2H, J=8.0 Hz), 7.45 (d, 2H, J=0.8 Hz), 8.42 (s, 1H). LRMS:279.2 (M+1).

The title compounds of Examples 65–77 were prepared by a method analogous to that described in Example 64.

EXAMPLE 65

5-(3-Chloro-4-fluoro-phenyl)-4-piperidin-1-yl-7H-pyrrolo[2,3-d]pyrimidine

Piperidine. LRMS: 331.8.

EXAMPLE 66

5-(4-Fluoro-phenyl)-4-piperidin-1-yl-7H-pyrrolo[2,3-d]pyrimidine

Piperidine. LRMS: 297.

EXAMPLE 67

5-(4-Chloro-phenyl)-4-piperidin-1-yl-7H-pyrrolo[2,3-d]pyrimidine

Piperidine. LRMS: 313.

EXAMPLE 68

5-(3,5-Bis-trifluoromethyl-phenyl)-4-piperidin-1-yl-7H-pyrrolo[2,3-d]pyrimidine

Piperidine. LRMS: 415.4.

EXAMPLE 69

4-Piperidin-1-yl-5-o-tolyl-7H-pyrrolo[2,3-d]pyrimidine

Piperidine. LRMS: 293.4.

EXAMPLE 70

4-Piperidin-1-yl-5-p-tolyl-7H-pyrrolo[2,3-d]pyrimidine

Piperidine. LRMS: 293.4.

EXAMPLE 71

5-(4-Methoxy-phenyl)-4-piperidin-1-yl-7H-pyrrolo[2,3-d]pyrimidine

Piperidine. LRMS: 309.4.

EXAMPLE 72

4-Piperidin-1-yl-5-(3-trifluoromethyl-phenyl)-7H-pyrrolo[2,3-d]pyrimidine

Piperidine. LRMS: 347.4.

EXAMPLE 73

5-(3-Chloro-phenyl)-4-piperidin-1-yl-7H-pyrrolo[2,3-d]pyrimidine

Piperidine. LRMS: 427.8.

EXAMPLE 74

3-(4-Piperidin-1-yl-7H-pyrrolo[2,3-d]pyrimidin-5-yl)-benzoic acid ethyl ester

Piperidine. LRMS: 465.4.

EXAMPLE 75

2-[3-(4-Piperidin-1-yl-7H-pyrrolo[2,3-d]pyrimidin-5-yl)-phenyl]-propan-2-ol

Piperidine. LRMS: 451.4.

EXAMPLE 76

4-(2-Methyl-piperidin-1-yl)-5-m-tolyl-7H-pyrrolo[2,3-d]pyrimidine 2-methylpiperidine. LRMS: 307.2.

EXAMPLE 77

4-Azepan-1-yl-5-m-Tolyl-7H-pyrolo[2,3-d]pyrimidine

Azepane. LRMS: 307.2.

EXAMPLE 78

METHOD O

4-Piperidin-1-yl-7H-pyrrolo[2,3-d]pyrimidine-5-carbonitrile

To a stirred solution of 4-chloro-7H-pyrrolo[2,3-d]pyrimidine-5-carbonitrile (54 mg/0.3 mmol) (prepared by the method of Townsend, et. al., J. Am. Chem. Soc., 1969, 91, 2102) suspended in 3.0 mL tert-Butanol was added piperidine (59 μL/0.60 mmol). The resulting mixture was then heated at reflux for 2.5 h and after cooling to room temperature, was transferred to a separatory funnel and diluted with ether (20 mL). The solution was extracted 2×10 mL with 1N HCl, the combined aqueous layers were adjusted to pH 7 with 2 N potassium hydroxide (KOH) solution forming a precipitate which was collected by filtration, washed with water and dried under reduced pressure to give 29 mg (42%) of the title compound as a colorless solid. Mp 209–211° C.; $^1$H NMR (400 MHz) (acetone-d6)δ: 1.72–1.74 (m, 6H), 3.72–3.79 (m, 4H), 8.12 (s, 1H), 8.29 (s, 1H). LRMS: 228 (M+1).

EXAMPLE 79

5-Ethynyl-4-piperidin-1-yl-7H-pyrrolo[2,3-d]pyrimidine

METHOD P

4-Chloro-5-iodo-7H-pyrrolo[2,3-d]pyrimidine

To a stirred solution of 4-chloro-7H-pyrrolo[2,3-d]pyrimidine (30 g/0.02 mol) dissolved in 80 mL of chloroform was added 4.5 grams (0.02 mol) of N-iodosuccinimide and the resulting mixture heated at reflux for 1 hour. After cooling to room temperature, the percipitate was removed by filtration and dried under reduced pressure affording 4.6 grams (82%) of the title compound.

METHOD Q

7-Benzenesulfonyl-4-chloro-5-iodo-7H-pyrrolo[2,3-d]pyrimidine

The title compound was prepared as previously described in Method L using the product from Method O affording 5.4 grams (80%) of material. LRMS: 419.6 (M+1), 279.7.

METHOD R

7-Benzenesulfonyl-5-iodo-4-piperidin-1-yl-7H-pyrrolo[2,3-d]pyrimidine

The title compound was prepared by the procedure described in Method M using the product from Method Q to produce the title compound. LRMS: 469 (M+1), 329.1.

METHOD S

7-Benzenesulfonyl-4-piperidin-1-yl-5-triethylsilanylethynyl-7H-pyrrolo[2,3-d]pyrimidine To a flamed-dried flask under nitrogen was charged 211 mg (0.5 mmol) of the product from Method R, 19 mg (0.1 mmol) of copper (I) iodide and 58 mg (0.05 mmol) of tetrakis(triphenylphosphine)palladium. To this mixture was then added 0.14 mL (1.0 mmol) of triethylamine and 0.27 mL (1.5 mmol) of triethylsilylacetylene as a solution in 1.5 mL of dry DMF. The resulting mixture stirred at room temperature for 3 hours, at which time, 5.0 mL of water were added and the mixture extracted with ethylacetate. The ethyl acetate extract was dried over $MgSO_4$ and concentrated in vacuo. The resulting crude product was then purified by silica-gel chromatography (7:1 hexanes/ethyl acetate) affording 194 mg (89%) of the title compound. LRMS: 481 (M+1), 341.

METHOD T

5-Ethynyl-4-piperidin-1-yl-7H-pyrrolo[2,3-d]pyrimidine

To a stirred solution of the product from Method S (194 mg/0.40 mmol) dissolved in 2.0 mL of dry THF was added dropwise 0.4 mL (0.4 mmol) of a 1 M solution of tetrabutylammonium fluoride in THF. The resulting mixture stirred at room temperature for 10 minutes, then was transferred to a methanol solution (3.0 mL) containing 1 gram of KOH, the new mixture stirred at room temperature for 15 minutes and concentrated in vacuo. The residue was partitioned between water and ethyl acetate, the ethyl acetate layer washed with water and brine, dried over $MgSO_4$ and concentrated to dryness in vacuo. The crude product was purified by silica-gel chromatography (2:1 ethyl acetate/hexanes) affording 72 mg (64%) of the title compound as a white crystalline solid. Mp 179–181° C. $^1$H NMR (400 MHz) (CDCl$_3$) d: 1.72 (br s, 6H), 3.20 (s, 1H), 3.82–3.83 (m, 4H), 7.47 (s, 1H), 8.35 (s, 1H). LRMS: 227 (M+1).

What is claimed is:

1. A compound of the formula

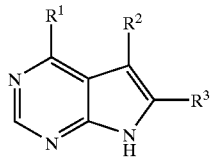

I or the pharmaceutically acceptable salt thereof; wherein $R^1$ is a group of the formula

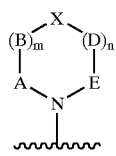

IV wherein m is 0, 1, 2 or 3;

n is 0, 1, 2 or 3;

X, B and D are each $CR^7R^8$;

A and E are each $CR^7R^8$; and $R^7$ and $R^8$ are each independently selected from the group consisting of hydrogen, deuterium, $(C_1-C_6)$alkyl, amino, hydroxy, $(C_1-C_6)$alkoxy, $(C_1-C_6)$alkylamino, $((C_1-C_6)$alkyl)amino, $(C_1-C_6)$acylamino, $(C_1-C_6)$acyl $(C_1-C_6)$alkylamino, $(C_1-C_6)$alkoxyacyl, $(C_1-C_6)$alkylaminoacyl, $((C_1-C_6)$alkyl)$_2$aminoacyl, aminoacyl, trifluoromethyl, trifluoromethyl$(C_1-C_6)$alkyl, $(C_1-C_6)$alkyl (difluoromethylene), $(C_1-C_3)$alkyl (difluoromethylene)$(C_1-C_3)$alkyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalhyl, $(C_3-C_6)$cycloalkyl$(C_1-C_6)$alkyl, hydroxy$(C_1-C_6)$alkyl, $(C_1-C_6)$acyloxy$(C_1-C_6)$alkyl, $(C_1-C_6)$alkoxy$(C_1-C_6)$alkyl, piperazinyl$(C_1-C_6)$alkyl, $(C_1-C_6)$acylamino$(C_1-C_6)$alkyl, piperidyl, $(C_1-C_6)$alkylpiperidyl, $(C_6-C_{10})$aryl$(C_1-C_6)$alkoxy$(C_1-C_6)$alkyl, $(C_5-C_9)$heteroaryl$(C_1-C_6)$alkoxy$(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, amino$(C_1-C_6)$alkyl, $(C_1-C_6)$alkylamino $(C_1-C_6)$alkyl, $((C_1-C_6)$alkyl)$_2$amino$(C_1-C_6)$alkyl, $R^{13}CO(C_1-C_6)$alkyl, $R^{13}CO(C_3-C_{10})$cycloalkyl, wherein $R^{13}$ is $R^{20}O$ or $R^{20}R^{21}N$ wherein $R^{20}$ and $R^{21}$ are each independently selected from the group consisting of hydrogen, $(C_1-C_6)$alkyl, $(C_6-C_{10})$aryl $(C_1-C_6)$alkyl and $(C_5-C_9)$heteroaryl$(C_1-C_6)$alkyl, $R^{14}$, $R^{14}(C_1-C_6)$alkyl, $R^{14}(C_3-C_{10})$cycloalkyl, wherein $R^{14}$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl or $(C_1-C_6)$acylpiperidyl, or a group of the formula

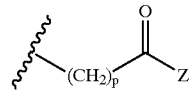

III wherein p is 0, 1, 2 or 3; and

Z is hydroxy, $(C_1-C_6)$alkoxy or $NR^1R^2$ wherein $R^1$ and $R^2$ are each independently selected from the group consisting of hydrogen, $(C_1-C_6)$alkyl, piperidyl, $(C_1-C_6)$alkylpiperidyl, $(C_6-C_{10})$arylpiperidyl, $(C_5-C_9)$heteroarylpiperidyl, $(C_6-C_{10})$aryl$(C_1-C_6)$alkylpiperidyl, $(C_5-C_9)$heteroaryl$(C_1-C_6)$alkylpiperidyl, $(C_1-C_6)$acylpiperidyl, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_6-C_{10})$aryl$(C_6-C_{10})$aryl, $(C_6-C_{10})$aryl$(C_6-C_{10})$aryl$(C_1-C_6)$alkyl, $(C_3-C_6)$cycloalkyl, $(C_3-C_6)$cycloalkyl$(C_1-C_6)$alkyl, $R^5(C_1-C_6)$alkyl, $(C_1-C_5)$alkyl$(CHR^5)(C_1-C_6)$alkyl, wherein $R^5$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl)$_2$ amino, $(C_1-C_6)$acylpiperazino, $(C_1-C_6)$ alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino, and $R^6(C_1-C_6)$alkyl, $(C_1-C_5)$alkyl$(CHR^6)(C_1-C_6)$alkyl, wherein $R^6$ is piperidyl, $(C_1-C_6)$alkylpiperidyl, $(C_6-C_{10})$arylpiperidyl, $(C_6-C_{10})$aryl$(C_1-C_6)$alkylpiperidyl, $(C_5-C_9)$heteroarylpiperidyl or $(C_5-C_9)$heteroaryl$(C_1-C_6)$alkylpiperidyl;

$R^2$ and $R^3$ are each independently selected from the group consisting of: hydrogen, deuterium, amino, halo, hydoxy, nitro, carboxy, $(C_2-C_6)$alkenyl, $(C_2-C_6)$alkynyl, trifluoromethyl, trifluoromethoxy, $(C_1-C_6)$alkyl, and $(C_1-C_6)$alkoxy wherein the alkyl or alkoxy groups are optionally substittued by one to three groups selected from halo, hydroxy, carboxy, amino $(C_1-C_6)$alkylthio, $(C_1-C_6)$alkylamino, $((C_1-C_6)$alkyl$)_2$amino, $(C_5-C_9)$heteroaryl, $(C_2-C_9)$heterocycloalkyl, $(C_3-C_9)$cycloalkyl or $(C_6-C_{10})$aryl; or $R^2$ and $R^3$ are each independently $(C_3-C_{10})$cycloalkyl, $(C_3-C_{10})$cycloalkoxy, $(C_1-C_6)$alkylamino, $((C_1-C_6)$alkyl$)_2$amino, $(C_6-C_{10})$arylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, $(C_1-C_6)$acyl, $(C_1-C_6)$alkoxy-CO—NH—, $(C_1-C_6)$alkyamino-CO—, $(C_5-C_9)$heteroaryl, $(C_2-C_9)$heterocycloalkyl or $(C_6-C_{10})$aryl wherein the heteroaryl, heterocycloalkyl and aryl groups are optionally substituted by one to three halo, $(C_1-C_6)$alkyl, $(C_1-C_6)$alkyl-CO—NH—, $(C_1-C_6)$alkoxy-CO—NH—, $(C_1-C_6)$alkyl-CO—NH—$(C_1-C_6)$alkyl, $(C_1-C_6)$alkoxy-CO—NH—$(C_1-C_6)$alkyl, $(C_1-C_6)$alkoxy-CO—NH—$(C_1-C_6)$alkoxy, carboxy, carboxy$(C_1-C_6)$alkyl, carboxy$(C_1-C_6)$alkoxy, benzyloxycarbonyl$(C_1-C_6)$alkoxy, $(C_1-C_6)$alkoxycarbonyl$(C_1-C_6)$alkoxy, $(C_6-C_{10})$aryl, amino, amino$(C_1-C_6)$alkyl, $(C_1-C_6)$alkoxycarbonylamino, $(C_6-C_{10})$aryl$(C_1-C_6)$alkoxycarbonylamino, $(C_1-C_6)$alkylamino, $((C_1-C_6)$alkyl$)_2$amino, $(C_1-C_6)$alkylamino$(C_1-C_6)$alkyl, $((C_1-C_6)$alkyl$)_2$amino$(C_1-C_6)$alkyl, hydroxy, $(C_1-C_6)$alkoxy, carboxy, carboxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxy-CO—NH—, $(C_1-C_6)$alkyl-CO—NH—, cyano, $(C_5-C_9)$heterocycloalkyl, amino-CO—NH—, $(C_1-C_6)$alkylamino-CO—NH—, $((C_1-C_6)$alkyl$)_2$amino-CO—NH—, $(C_6-C_{10})$arylamino-CO—NH—, $(C_5-C_9)$heteroarylamino-CO—NH—, $(C_1-C_6)$alkylamino-CO—NH—$(C_1-C_6)$alkyl, $((C_1-C_6)$alkyl$)_2$amino-CO—NH—$(C_1-C_6)$alkyl, $(C_6-C_{10})$arylamino-CO—NH—$(C_1-C_6)$alkyl, $(C_5-C_9)$heteroarylamino-CO—NH—$(C_1-C_6)$alkyl, $(C_1-C_6)$alkylsulfonyl, $(C_1-C_6)$alkylsulfonylamino, $(C_1-C_6)$alkylsulfonylamino$(C_1-C_6)$alkyl, $(C_6-C_{10})$arylsulfonyl, $(C_6-C_{10})$arylsulfonylamino, $(C_6-C_{10})$arylsulfonylamino$(C_1-C_6)$alkyl, $(C_1-C_6)$alkylsulfonylamino, $(C_1-C_6)$alkylsulfonylamino$(C_1-C_6)$alkyl, $(C_5-C_9)$heteroaryl or $(C_2-C_9)$heterocycloalkyl;

with the proviso that when $R^2$ and $R^3$ are each independently hydrogen or $(C_1-C_6)$alkyl, $R^1$ cannot be unsubstituted piperidinyl; and with the proviso that when $R^2$ and $R^3$ are each hydrogen, $R^1$ cannot be unsubstituted pyrrolidinyl.

2. A compound selected from the group consisting of:

5-Fluoro-4-piperidin-1-yl-7H-pyrrolo[2,3-d]pyrimidine;

4-Piperidin-1-yl-5-trifluoromethyl-7H-pyrrolo[2,3-d]pyrimidine;

N,N-Dimethyl-N'-[3-(4-piperidin-1-yl-7H-pyrrolo[2,3-d]pyrimidin-5-yl)-benzyl]-ethane-1,2-diamine;

2-[1-(5-m-Tolyl-7H-pyrrolo[2,3-d]pyrimidin-4-yl)-piperidin-4-yl]-ethanol;

5-(3-Isopropyl-phenyl)-4-piperidin-1-yl-7H-pyrrolo[2,3-d]pyrimidine;

5-(3-Methyl-3H-imidazol-4-yl)-4-piperidin-1-yl-7H-pyrrolo[2,3-d]pyrimidine;

5-(1-Methyl-1H-imidazol-4-yl)-4-piperidin-1-yl-7H-pyrrolo[2,3-d]pyrimidine;

5-(2-Methyl-pyridin-4-yl)-4-piperidin-1-yl-7H-pyrrolo[2,3-d]pyrimidine;

5-Chloro-4-piperidin-1-yl-7H-pyrrolo[2,3-d]pyrimidine;

5-Ethynyl-4-piperidin-1-yl-7H-pyrrolo[2,3-d]pyrimidine;

4-Piperidin-1-yl-5-m-tolyl-7H-pyrrolo[2,3-d]pyrimidine; and 4-(3,3-Dimethyl-piperidin-1-yl)-7H-pyrrolo[2,3-d]pyrimidine;

or a pharmaceutically acceptable salt thereof.

3. A compound according to claim 1, wherein $R^2$ and $R^3$ are each independently selected from the group consisting of hydrogen, $(C_1-C_6)$alkyl, $(C_1-C_6)$alkoxy, $(C_3-C_{10})$cycloalkyl, $(C_3-C_{10})$cycloalkoxy, $(C_2-C_9)$heterocycloalkyl, $(C_5-C_9)$heteroaryl or $(C_6-C_{10})$aryl.

* * * * *